(12) United States Patent
Weinberg et al.

(10) Patent No.: US 10,985,383 B2
(45) Date of Patent: Apr. 20, 2021

(54) SCALABLE, MASSIVELY PARALLEL PROCESS FOR MAKING MICRO-SCALE FUNCTIONAL PARTICLES

(71) Applicant: Weinberg Medical Physics, Inc., North Bethesda, MD (US)

(72) Inventors: Irving N. Weinberg, North Bethesda, MD (US); Lamar Odell Mair, Baltimore, MD (US)

(73) Assignee: Weinberg Medical Physics, Inc., North Bethesda, MD (US)

( * ) Notice: Subject to any disclaimer, the term of this patent is extended or adjusted under 35 U.S.C. 154(b) by 0 days.

(21) Appl. No.: 15/842,135

(22) Filed: Dec. 14, 2017

(65) Prior Publication Data
US 2018/0108921 A1    Apr. 19, 2018

Related U.S. Application Data (62) Division of application No. 14/922,907, filed on Oct. 26, 2015, now Pat. No. 9,865,887.

(60) Provisional application No. 62/068,083, filed on Oct. 24, 2014.

(51) Int. Cl.
| | | |
|---|---|---|
| H01M 8/02 | (2016.01) | |
| H01M 8/1097 | (2016.01) | |
| H01M 8/22 | (2006.01) | |
| H01M 4/88 | (2006.01) | |
| H01M 8/0221 | (2016.01) | |
| A61K 41/00 | (2020.01) | |
| H01M 8/1018 | (2016.01) | |

(52) U.S. Cl.
CPC .......... *H01M 8/02* (2013.01); *A61K 41/0052* (2013.01); *H01M 4/8853* (2013.01); *H01M 8/0221* (2013.01); *H01M 8/1097* (2013.01); *H01M 8/22* (2013.01); H01M 2008/1095 (2013.01); H01M 2250/30 (2013.01); Y02B 90/10 (2013.01); Y02P 70/50 (2015.11)

(58) Field of Classification Search
CPC .... H01M 8/02; H01M 4/8853; H01M 8/1097; H01M 8/22; A61K 41/0052
See application file for complete search history.

(56) References Cited

U.S. PATENT DOCUMENTS

| | | | |
|---|---|---|---|
| 7,132,039 B2 * | 11/2006 | Anazawa | B82Y 30/00 204/173 |
| 7,249,604 B1 * | 7/2007 | Mohanraj | A61B 17/12022 128/898 |
| 2012/0186981 A1 | 7/2012 | Achterhoff et al. | |

FOREIGN PATENT DOCUMENTS

KR        101076609        * 10/2011

OTHER PUBLICATIONS

Woo et al. KR 101076609, published: Oct. 2011, English machine translation obtained on Oct. 23, 2020. (Year: 2011).*
Zhang et al.: Silicon dioxide nanotubes prepared by anodic alumina as templates; Journal of Materials Research, vol. 15(2), 2000.
Y. Yoo, et al.: Electrochemically Fabricated Zero-Valent Iron, Iron-Nickel, and Iron-Palladium Nanowires for Environmental Remediation Applications; Water Science & Technology, vol. 55(1-2), pp. 149-156, 2007.
Chen et al.: Plasmonic Focusing in Rod-Sheath Heteronanostructures; journal ACS Nano, vol. 3, No. 1, pp. 87-92, 2009.
Cosnier et al.: Towards glucose biofuel cells implanted in the human body for powering artificial organs: Review; Electrochemistry Communications, vol. 38, pp. 19-23, 2014.
Masuda et al.; Self-ordering of cell configuration of anodic porous alumina with large-size pores in phosphoric acid solution; published in the Japanese Journal of Applied Physics, vol. 37, 1998.
Rapoport et al.: A Glucose Fuel Cell for Implantable Brain-Machine Interfaces; in PLoS ONE, vol. 7(6), e38436, 2012.
Penner et al.: Preparation and Electrochemical Characterization of Ultramicroelectrode Ensembles; Analytical Chemistry, vol. 59, pp. 2625-2630, 1987.

* cited by examiner

*Primary Examiner* — Genevieve S Alley
(74) *Attorney, Agent, or Firm* — Barnes & Thornburg LLP (57) ABSTRACT

A method of fabrication produces one or more functional microparticles using a parallel pore working piece. In one embodiment, the method forms a particle that includes a segment for the oxidation of a biofuel (such as glucose) and the reduction of oxygen. The particle may be synthesized in a structure with defined and parallel, uniform, thin pores that completely penetrate the structure. Further, the functional microparticle may be configured to reside in a human or animal body or cell such that it may be self-contained fuel cell having an anode, a cathode, a separator membrane, and a magnetic component. In other embodiments, the functional microparticles may deliver energy or therapeutic materials in the body.

11 Claims, 8 Drawing Sheets

SCALABLE, MASSIVELY PARALLEL PROCESS FOR MAKING MICRO-SCALE FUNCTIONAL PARTICLES

CROSS-REFERENCE

This application is a divisional application of U.S. application Ser. No. 14/922,907 filed on Oct. 26, 2015, and claims priority under 35 U.S.C. 119(e) to U.S. Provisional Patent Application No. 62/068,083 (incorporated by reference in its entirety) filed on Oct. 24, 2014, entitled "SCALABLE, MASSIVELY PARALLEL PROCESS FOR MAKING MICRO-SCALE PARTICLES THAT INCORPORATE A FUEL CELL."

FIELD

Disclosed embodiments are directed to functional microparticles and method of fabrication of functional microparticles.

SUMMARY

Disclosed embodiments are directed to functional microparticles and methods of fabrication of functional microparticles using a parallel pore working piece. For the purpose of this specification, functional microparticles are defined as devices with one dimension less than fifty microns in length, and which exhibit functionality such as the ability to generate electrical current (e.g., as a fuel cell), radiofrequency wave generation (e.g., as a spin-transfer nano-oscillator), or carry a therapeutic payload (e.g., as a drug delivery vehicle), or deliver therapeutic energy (e.g., as a magnetizable particle exposed to an alternating magnetic field), or a combination of such functionalities.

In accordance with at least one embodiment, such a functional microparticle may be configured to reside in a human or animal body or cell. The functional microparticle may be a self-contained fuel cell having an anode, a cathode, a separator membrane, and a magnetic component.

In accordance with at least one embodiment, such a device may include segments for the oxidation of a biofuel (such as glucose) and the reduction of oxygen.

In accordance with at least one embodiment, the particle may be synthesized in a structure with defined and parallel, uniform, thin pores that completely penetrate the structure.

BRIEF DESCRIPTION OF THE FIGURES

The detailed description particularly refers to the accompanying figures in which:

FIGS. 1-8 collectively illustrate a process for the scalable synthesis of a single functional microparticle, wherein the process is shown as a cross-section of a parallel pore working piece, in accordance with disclosed embodiments.

DETAILED DESCRIPTION

For the purposes of this description, a fuel cell is provided as an example of a functional microparticle. It is understood that many or all of the processes specified herein may apply to the production and description of functional microparticles other than fuel cells, whether or not the term "fuel cell" is specifically used in the description.

Fuel cells are devices that convert chemical energy into electrical energy via the catalysis of reduction and oxidation reactions. Glucose fuel cells have been proposed as useful devices for powering electronics inside the bodies of humans and other animals.

Several investigators have performed experiments demonstrating the application of implantable glucose fuel cells in various animals, including dogs, sheep, rats snails, lobsters, and cockroaches. Some of these examples are reviewed in the publication "Towards glucose biofuel cells implanted in the human body for powering artificial organs: Review", by Serge Cosnier, Alan Le Goff, and Michael Holzinger, in Electrochemistry Communications, Volume 38, pages 19-23, 2014 (incorporated herein by reference in its entirety).

The processes involved in a fuel cell placed in the body include the oxidation of a fuel material in the body at an anode, and the reduction of oxygen at a cathode. In an implantable glucose fuel cell, the fuel material being oxidized is glucose. Other types of fuel cells may oxidize other materials. Connecting the anode and cathode surfaces across a resistive load enables the flow of electrons, which can power another device or component of a device or activate one or more biological cells in the body (e.g., neurons, muscle cells).

Disclosed embodiments provide a device comprised of a particulate fuel cell that can reside in a human or animal body or cell, and a process for making such devices. This device may be a self-contained fuel cell having an anode, a cathode, a separator membrane, and a magnetic component. The device, in the form of a particle, may include segments for the oxidation of a material in the body (such as glucose) and the reduction of oxygen.

Figure 1:
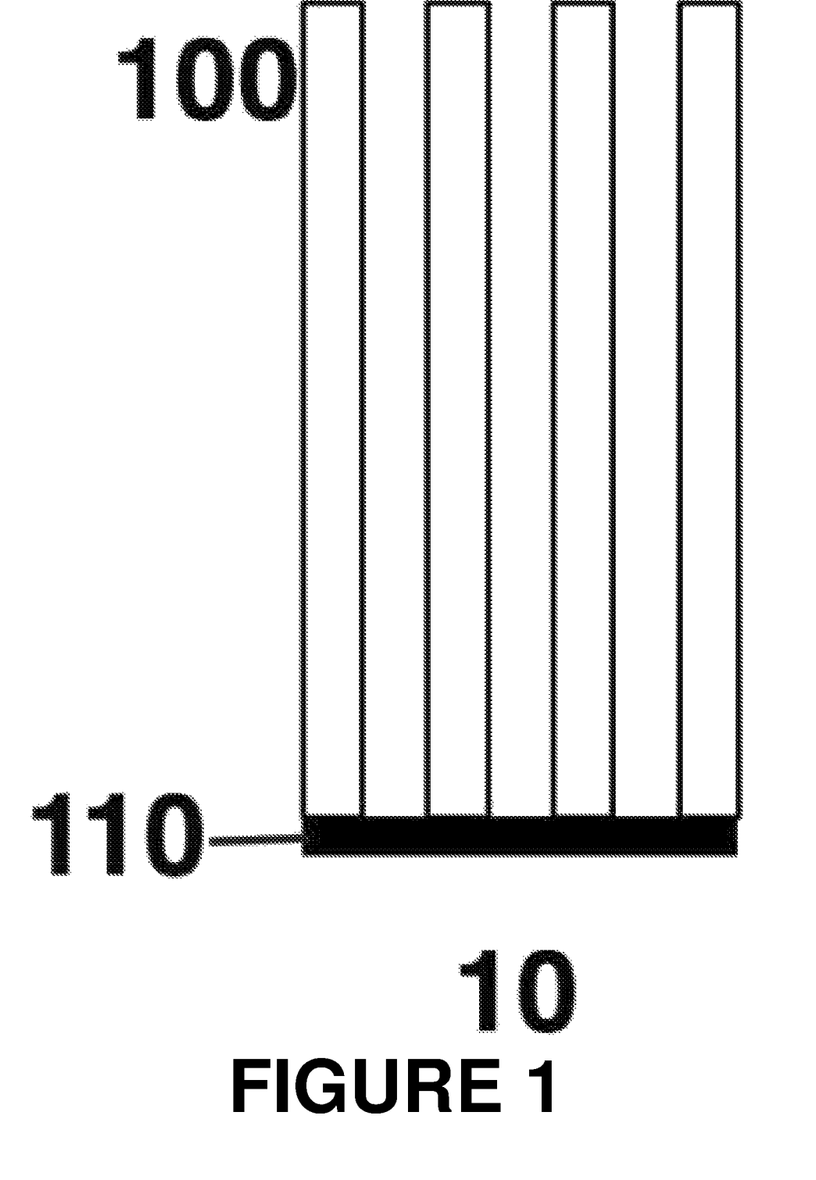
FIG. 1 illustrates fabrication operations of preparing a parallel pore working piece for electroplating in accordance with the disclosed embodiments.

In accordance with at least one embodiment, the particle may be synthesized in a structure with defined and parallel, uniform, thin pores that completely penetrate the structure 100, as illustrated in FIG. 1.

One example of the structure 100 may be a parallel pore working piece containing pores. The terms "working piece" and "parallel pore working piece" are intended to refer to a template that is used to fabricate particles, said template later being either discarded or re-used.

In one embodiment, this parallel pore working piece may be an anodized aluminum oxide nanoporous filter membrane. In another embodiment, the parallel pore working piece may be a polycarbonate track etched filter membrane. An important aspect of the parallel pore working piece is that it is a component containing many pores.

In one embodiment in which the working piece is an anodized aluminum oxide nanoporous filter membrane, the pore density may be as large as one billion pores per square centimeter. Because the working piece contains many pores, and because the method used for making fuel cells using such a working piece addresses many pores at a time, the method is massively parallel. As a result, the method may simultaneously generate billions of functional microparticles, with each pore of the parallel pore working piece containing a single functional microparticle.

In accordance with at least one embodiment, a parallel pore working piece may be implemented using an Anodic Aluminum Oxide (AAO) filter membrane. A method for making AAO filter membranes with uniform, parallel pores was taught by H. Masuda, K. Yada, and A. Osaka, in their publication "Self-ordering of cell configuration of anodic porous alumina with large-size pores in phosphoric acid solution," published in the Japanese Journal of Applied Physics, Volume 37, 1998 (incorporated herein by reference in its entirety).

The AAO may be used as the working pieces for generating fuel cells, the resulting fuel cells may be cylindrical in shape. In one embodiment of the invention, the fuel cell may contain material layers nested within one another.

FIGS. 1-8 collectively illustrate a process for the scalable synthesis of a single microwire glucose fuel cell, wherein the process is shown as a cross-section of the parallel pore working piece 100 and single microwire fuel cell. For the purpose of this disclosure, the term "microwire" is defined as a structure where the radius is less than fifty microns.

As illustrated in FIG. 1, the fabrication of the functional microparticle may begin at operation 10. FIG. 1 illustrates that the applied conductive layer 110 seals an opening of the pores of the working piece. Sealing one side of the working piece may be accomplished by applying a metal film 110 to one side of the parallel pore working piece. Said application also prepares the working piece for electroplating.

In accordance with at least one disclosed embodiment, a pore wetting process may be performed by submerging the entire parallel pore working piece in water and applying sonication to the parallel pore working piece. During the pore wetting process, the act of sonicating the template provides the necessary mechanical energy for a solution to enter the potentially narrow diameter pores of the working piece. In one embodiment of the disclosure, the wetting process overcomes the surface tension which may exist at the openings of the pores. When surface tension is high near the pore openings, the pore wetting process facilitates the entry of liquid into the pores of the working piece. The application of a metal film 110 to one side of the parallel pore working piece may result in a structure composed of parallel pores spanning the length of a working piece, where the pores are sealed closed on one side.

Figure 2:
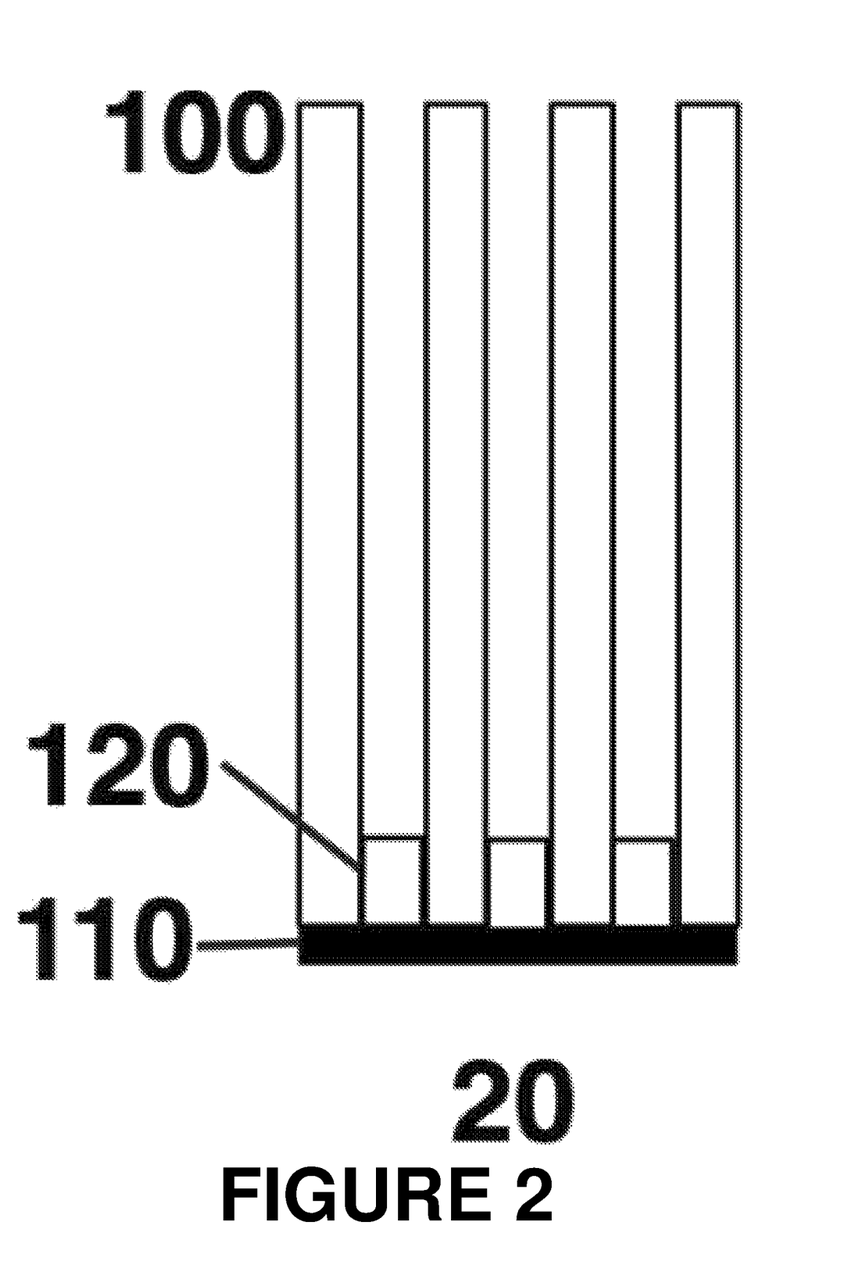
FIG. 2 illustrates fabrication operations for electrodeposition of a conductive layer into pores of the parallel pore working piece by exposing the open pore side of the parallel pore working piece to an electrolyte in accordance with disclosed embodiments.

Further fabrication may proceed as illustrated in FIG. 2, wherein, at 20, electroplating a conductive layer 120 into the pores of the parallel pore working piece. With sealed pores on one side, a conductive layer 120 may then be electroplated into the pores of the working piece, as illustrated in FIG. 2.

FIG. 2 illustrates fabrication operations for electrodeposition of a conductive layer 120 into pores of the parallel pore working piece by exposing the open pore side of the parallel pore working piece to an electrolyte. Magnetic materials may be deposited in this operation in order to confer functionality.

The conductive layer 120 acts as a conductive surface for further electrodeposition and processing, and/or may also act as a magnetic material segment for magnetic field manipulation of the functional microparticle. The magnetic material segment may be composed of a ferromagnetic material, such as iron, nickel, or cobalt. The magnetic material segment may be composed of a paramagnetic or superparamagnetic material, such as magnetite or maghemite. The magnetic manipulation may occur in the course of the fabrication process, for example, in order to move particles from one section of a chamber to another. As a result of the above-described fabrication methodology, disclosed embodiments may be used to produce a device wherein a magnetic iron-palladium segment 120 is attached to the platinum anode 130. In one embodiment, the iron-palladium segment is grown, and is in direct contact with the electrically conductive sealing layer 110 of the working piece. This iron-palladium segment 120 may be composed of any electrically conductive layer.

At 20, electrodeposition into the pores of the working piece may be accomplished by exposing the open pore side of the membrane to an electrolyte (for example, a nickel plating solution consisting of 1.1M nickel sulfate hexahydrate, 0.2M nickel chloride hexahydrate, and 0.75M boric acid). In electroplating materials onto the side of metal film 110 inside the pores of the parallel pore working piece 100, as taught in the publication "Preparation and Electrochemical Characterization of Ultramicroelectrode Ensembles", Penner et al. published in Analytical Chemistry, Volume 59, pages 2625-2630, 1987 (incorporated by reference herein in its entirety), the electroplating process may fill the pores entirely with the material being plated, or may partially fill the pores with the material being plated.

The operation performed at 20 may involve the electroplating of a palladium-iron alloy 120, as taught by B.-Y. Yoo, et al. in their publication "Electrochemically Fabricated Zero-Valent Iron, Iron-Nickel, and Iron-Palladium Nanowires for Environmental Remediation Applications", in Water Science & Technology, Volume 55(1-2), pages 149-156, 2007 (incorporated by reference herein in its entirety).

Figure 3:
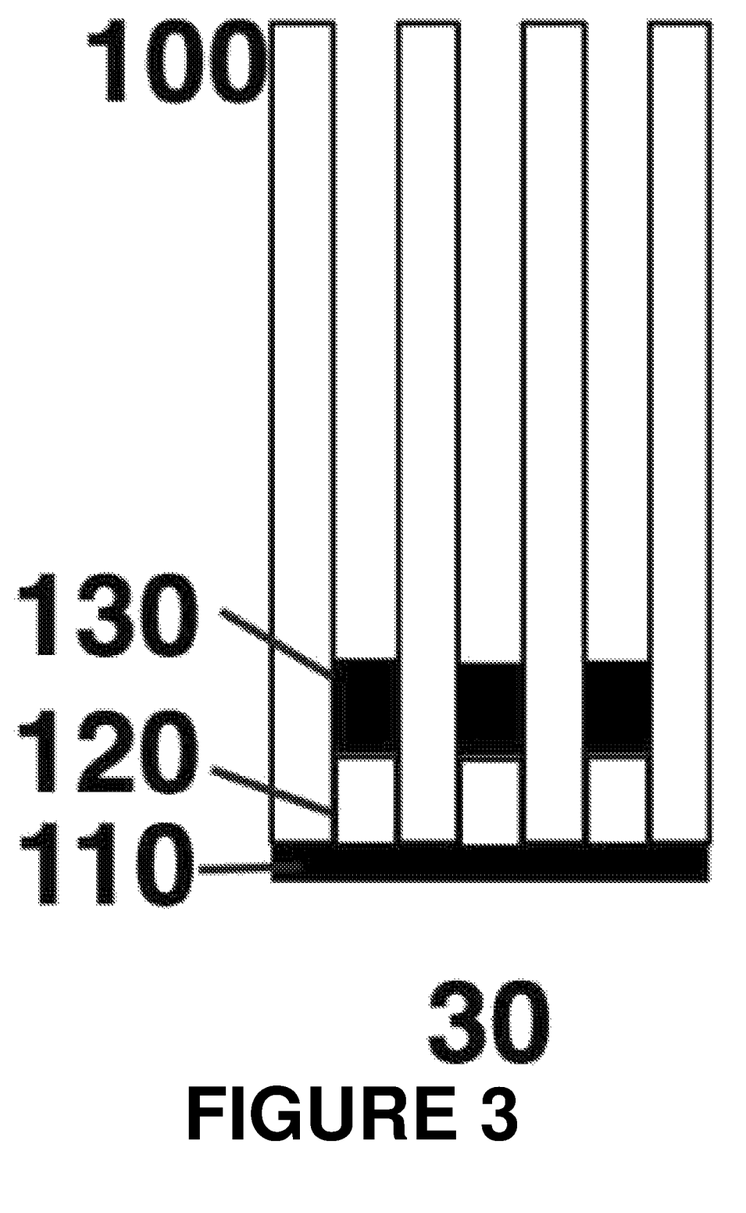
FIG. 3 illustrates fabrication operations for electrodeposition of an anode onto the conductive pore-sealing layer, in accordance with disclosed embodiments.

Fabrication operations may then proceed to 30, illustrated in FIG. 3, at which electrodeposition of an anode 130 onto the electrodeposited conductive layer 120 is performed.

In one embodiment, the anode is made of platinum. In accordance with at least one embodiment, iron-palladium 120 may be deposited. This platinum anode layer 130 may also fill the width of the pore. The iron-palladium is an example of a magnetizable material that may be used to propel or position the particle using magnetic fields. In the interest of brevity, it is understood that layer 130 may represent a combination of materials, either deposited in a single operation (for example by using an electroplating solution with multiple metals), or in multiple operations (for example, by successively using electroplating solutions with multiple metals).

It is understood that the deposited metallic layers may be arrayed to form a spin-torque nano-oscillator or similar spintronic device, which converts electrical current into radiofrequency waves. It is understood that similarly deposited layers may confer diverse functionality, for example by acting as diodes, rectifiers, transistors, resistors, capacitors, etc.

Figure 4:
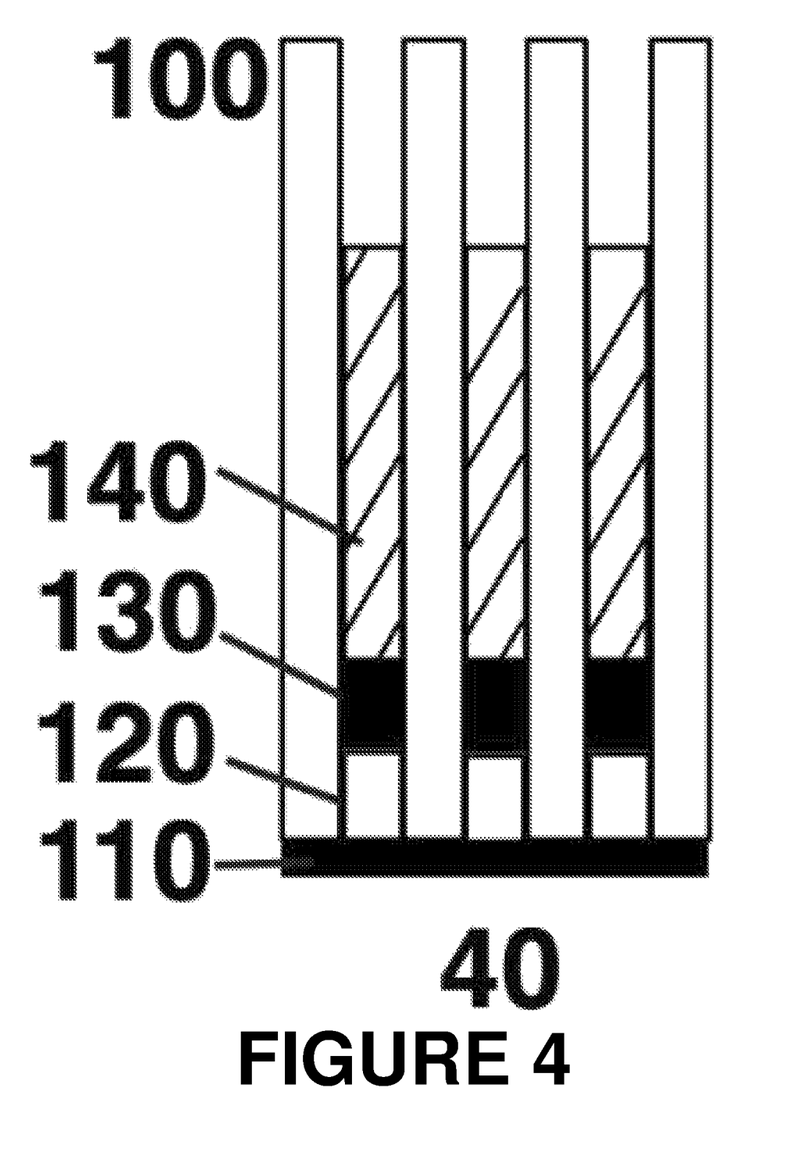
FIG. 4 illustrates fabrication operations for vacuum-assisted filling of a polymer, ceramic, or composite separator membrane into the pores of the parallel pore working piece and onto the previously deposited anode, in accordance with disclosed embodiments.

Fabrication operations may then proceed to 40, as illustrated in FIG. 4, at which deposition of a polymer, ceramic, or composite separator membrane 140 may be performed into the pores of the parallel pore working piece 100, and onto the previously deposited layer 130. Said deposition may be performed with vacuum-assisted filling, as taught by X. Chen, S. Li, C. Xue, M. J. Banholzer, G. C. Schatz, and C. Mirkin, in their publication "Plasmonic Focusing in Rod-Sheath Heteronanostructures," published in the journal ACS Nano, Volume 3, Number 1, pages 87-92, 2009 (incorporated by reference herein in its entirety).

In a fuel cell, a separator membrane operates as a barrier, separating gases generated at the anode and cathode of the fuel cell. The separator membrane also acts to electrically insulate the anode from the cathode and prevent the fuel cell from shorting between the anode and cathode. This separator membrane may allow the passage of a fuel material (e.g., glucose) but inhibit the passage of oxygen molecules. In at least one embodiment, vacuum-assisted filling may be performed by depositing a diluted polymer separator membrane material (for example, Nafion dissolved in a solvent) into the open pores of the parallel pore working piece. Nafion has been previously studied as a separator membrane for glucose fuel cells, as taught by Benjamin I. Rapoport, Jakub T. Kedzierski, and Rahul Sarpeshkar in their publication entitled "A Glucose Fuel Cell for Implantable Brain-Machine Interfaces," in PLoS ONE, Volume 7(6), e38436, 2012 (incorporated by reference herein in its entirety).

Some of the materials used in the fuel cells may begin as liquids or dispersions, becoming solids in the process of making the fuel cells. In one embodiment, a relevant fuel cell material may be dispersed in a solvent, forming a solution. This process may useful for the deposition of any layer in the fuel cells, including the layers depicted in FIGS. 1, 2, 3, 4, 6, and 7. A liquid volume of this solution containing a relevant fuel cell component material may be deposited onto the open pores of the working piece. By depositing a the relevant fuel cell component in a solvent on the open pore side of the working piece (the side of the working piece that is not sealed), placing the working piece in a vacuum chamber, and evacuating the chamber, the solvent may be evaporated, leaving the relevant fuel cell material deposited in the pores of the working piece. In one embodiment, the vacuum is applied to all sides of the working piece.

Applying vacuum to the parallel pore working piece may perform at least two functions. One function is to draw the deposited separator membrane 140 solution into the pores of the parallel pore working piece. Another function of the vacuum-assisted filling operation is to evaporate the solvent in which the separator membrane 140 material (polymer, ceramic, or composite) is dissolved. Thus, the vacuum process serves to pull a solution, containing a solute and a solvent, sitting on the open pores of the working piece and allow for deposition of the solute in the pores of the working piece as the solvent is evaporated. The result is that the solute remains, and is drawn into the pores of the working piece due to the applied vacuum. The result of this vacuum-assisted filling is a set of cylinders 140, 170 within the same pore, these ensembles of cylinders being made massively parallel using pores of the parallel pore working piece 100.

Figure 5:
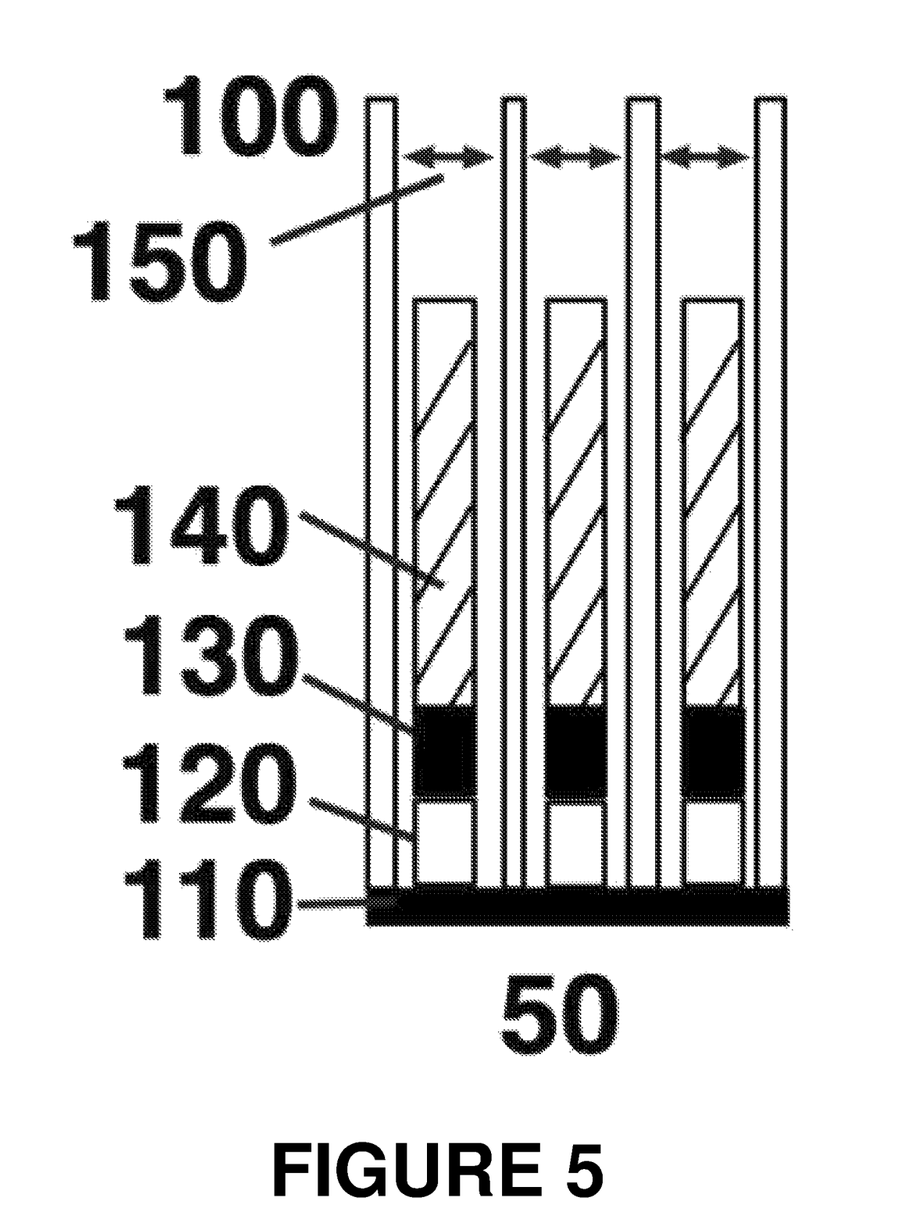
FIG. 5 illustrates fabrication operations for widening the parallel pore working piece pores by etching the parallel pore working piece material, in accordance with disclosed embodiments.

Fabrication operations may then proceed to 50, as illustrated in FIG. 5, at which the pores of the parallel pore working piece are widened by etching 150 the parallel pore working piece material 100. In FIG. 5, item 150 refers to the process of widening the pores of the working piece by chemically etching the working piece pore walls. During the etching process 150, the pores of the working piece are enlarged. Etching the pores to increase pore diameter, resulting in a gap between the walls of the pores and the layers of deposited materials 120, 130, 140. In at least one embodiment, this operation 50 may be accomplished using an aqueous solution of sodium hydroxide to etch the pores of an AAO parallel pore working piece 100.

In at least one disclosed embodiment, the sodium hydroxide may etch the full length of the pores, making them 10% to 50% wider than the original pore diameters. Etching the pores of the working piece does not involve etching the layers deposited into the pores of the working piece 120, 130, 140, 170.

Figure 6:
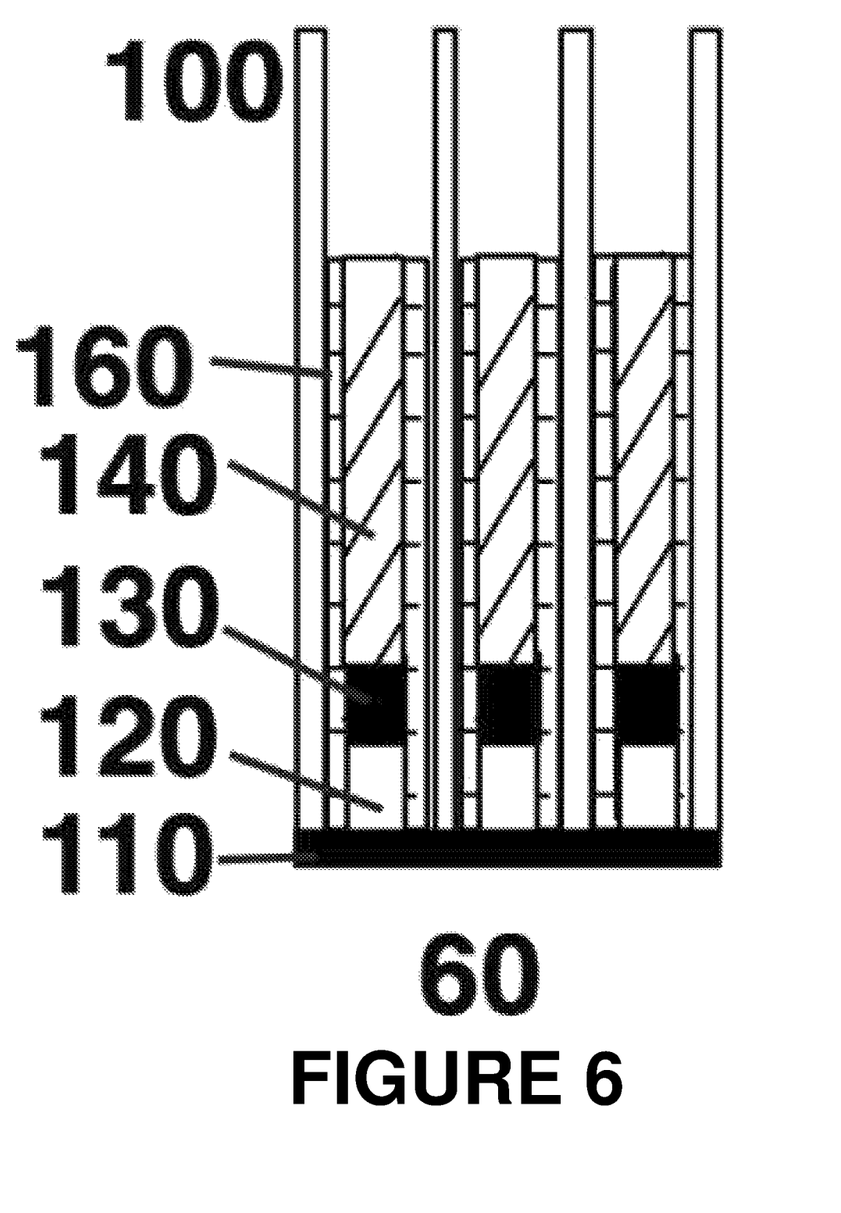
FIG. 6 illustrates fabrication operations for generating an insulating tube within the pores of the parallel pore working piece, in accordance with disclosed embodiments.

Fabrication operations may then proceed to 60, as illustrated in FIG. 6, at which point an insulating tube 160 is generated within the pores of the parallel pore working piece 100. As shown in FIG. 6, after the widening of the pores shown in FIG. 5, an insulating layer 160 may be deposited into the pores, filling the space between the sidewalls of the working piece pore and the previously deposited segments of the fuel cell (120, 130, 140). Thus, FIG. 6 illustrates fabrication operations for generating an insulating tube within the pores of the parallel pore working piece. Delivery functionality may be conferred by having the tube carry therapeutic payloads, for example drugs, cells, genetic material or RNA or siRNA fragments.

In one embodiment of the invention, the insulating tube is generated by placing a solution of silicon dioxide sol-gel on the open pores of the working piece, then applying a vacuum to move the sol-gel into the pores of the working piece. The tube 160 is shown in cross section in FIG. 6, however the image is intended to show that the tube surrounds all previously grown segments of the fuel cell. The tube is formed from an electrically insulating material. In one embodiment of the invention, the tube is formed from silicon dioxide deposited from a sol-gel, inserted into the pores by deposition using vacuum pressure.

In accordance with at least one embodiment, the insulating tube 160 may cover the sidewalls of the pores only; alternatively, it may cover more or less. The sidewalls of the pores are defined as the surfaces of the working piece which are interior to the pores. Note that the sidewalls of the pores do not include materials 120, 130, 140, 170 that have been deposited into the pores of the working piece.

The height of the insulating tube 160 may be equivalent to the sum of the length of the previously grown layers. Such a height specification is useful, as an insufficiently tall insulating tube may result in an exposed region of the fuel cell, and thus may result in an electrical short in the device. It is possible that the insulating tube is deposited with the assistance of a vacuum, as discussed above. In at least one embodiment, the material forming tube 160 is a sol-gel formulation of silicon dioxide, as taught by M. Zhang, Y. Bando, and K. Wada in their publication "Silicon dioxide nanotubes prepared by anodic alumina as templates", in the Journal of Materials Research, Volume 15(2), 2000 (incorporated herein by reference in its entirety). In such an embodiment, silicon dioxide sol-gel may be deposited into the widened pores 150 of the parallel pore working piece 100 by dipping the parallel pore working piece into a silicon oxide sol-gel, and then applying vacuum to the particles. Here the application of a vacuum occurs after the working piece is dipped into the solution containing the sol-gel. It is also possible to apply the sol-gel to the open pores side of the working piece, and subsequently apply a vacuum.

In the fabrication operations at 60, as illustrated in FIG. 6, the role of applying vacuum may be to pull the sol-gel into the pores of the template, as well as to remove the solvent from the solution by evaporation. The solution referred to here is the solution containing a solvent and a solute, the solute being the material that is deposited into the widened pores of the working piece. A typical sol-gel solution is composed of silicon dioxide and tetraethyl orthosilicate. Thus, the insulating layer 160 material may flow around the separator membrane 140. The insulating layer 160 may electrically insulate the separator membrane 140 from the local surrounding environment of the fuel cell particle.

Figure 7:
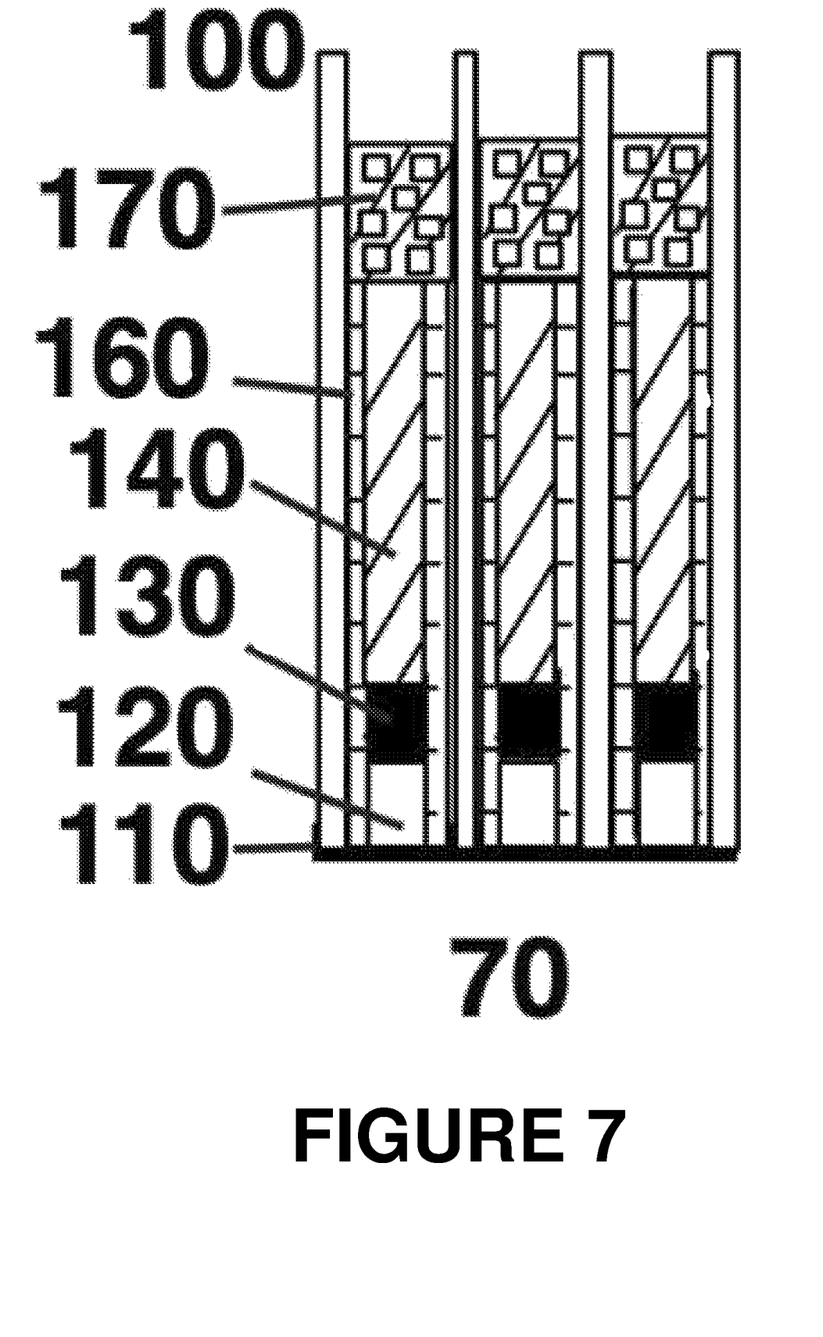
FIG. 7 illustrates fabrication operations for performing deposition of a cathode in accordance with disclosed embodiments, wherein an oxygen-reducing agent is dispersed in a separator membrane material that allows the passage of a fuel substrate (e.g., glucose) but inhibits the passage of oxygen molecules.

It is understood that the tube section 160 may function as a carrier of therapeutic materials, which may enter the tube section in a subsequent operation instead of proceeding to operation 70.

Fabrication operations may then proceed to 70, as illustrated in FIG. 7, at which a cathode 170 is deposited (deposition), wherein an oxygen-reducing agent is dispersed in a separator membrane material that allows the passage of glucose but inhibits the passage of oxygen molecules. FIG. 7 illustrates fabrication operations for performing deposition of a cathode, wherein an oxygen-reducing agent is dispersed in a separator membrane material that allows the passage of a fuel substrate (e.g., glucose) but inhibits the passage of oxygen molecules.

As taught by B. I. Rapoport, J. T. Kedzierski, and R. Sharpeshkar in their publication "A Glucose Fuel Cell for Implantable Brain-Machine Interfaces," published in PLoS ONE, Volume 7, Issue 6, June 2012, this material may be a composite of carbon nanotubes and nafion polymer. The primary role of this material is to reduce oxygen and allow for the passage of the fuel molecule, such as glucose.

In accordance with at least one embodiment, the cathode 170 may be a composite of Nafion/graphene, Nafion/carbon nanotubes, or Nafion/C60 (Buckminsterfullerene).

The Nafion/graphene, Nafion/carbon nanotube, or Nafion/C60 composite may also be deposited via vacuum-assisted filling into the open pores of the parallel pore working piece 100. In accordance with at least one embodiment, the parallel pore working piece 100 may be dissolved using sodium hydroxide at a concentration between 1 mM and 10M. Dissolution of the parallel pore working piece 100 may result in free-floating microscale glucose fuel cells.

Figure 8:
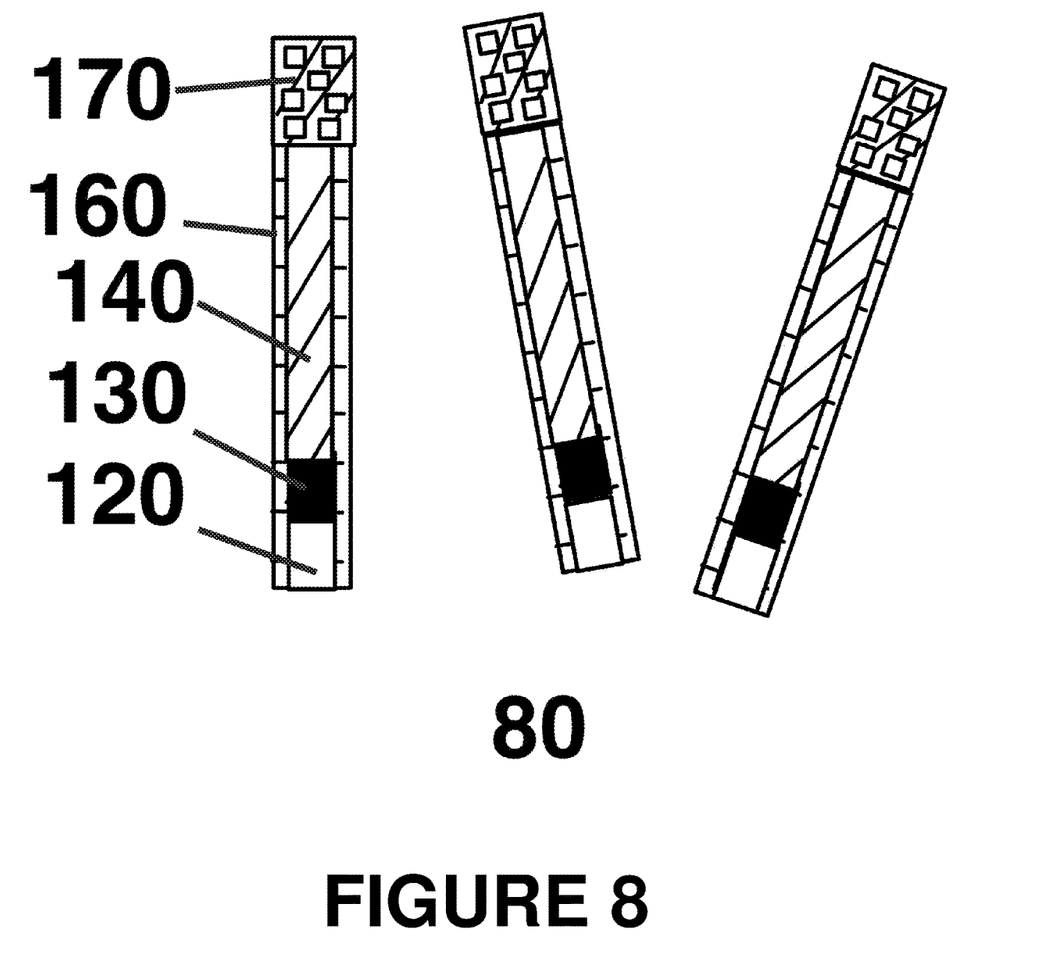
FIG. 8 illustrates release of the particles from the working piece, which has been etched away, in accordance with disclosed embodiments.

FIG. 8 shows the fuel cells after being released from the working piece. Etching the working piece releases the particles from the templates. After releasing the particles from the working piece, the particles can be dispersed in liquids or dried onto surfaces.

In the resulting device, the conducting layers of the anode and cathode may be separated from the cathode 170 by the separator membrane 140 that allows for the passage of glucose, but may inhibit the passage of oxygen. This type of membrane is commonly referred to as a "proton exchange membrane;" at least one embodiment may use the commercially available product Nafion as the material of choice.

In the disclosed embodiments, glucose may be oxidized at the platinum anode 130 and oxygen may be reduced at the cathode 170. These two reactions may continue in the presence of a fuel source such as glucose. Nevertheless, in accordance with at least one embodiment, the buildup of charge may be accompanied by a resulting electric field.

If a fuel cell's acquired energy is not discharged across a load, the fuel cell may build up electrical charge at the anode and cathode. If the charge is not quenched, it may be used to perform various functions within the bodies of humans or other animals. In accordance with at least one embodiment, this electric field may be used to guide neuronal regrowth, as taught in U.S. patent application Ser. No. 14/874,857, entitled "METHOD AND APPARATUS FOR IMAGE-DIRECTED NERVE GROWTH," filed Oct. 1, 2015 (incorporated herein by reference in its entirety herein) or to otherwise stimulate neuronal or other cells.

In accordance with at least one embodiment, some component of the fuel cell incorporates a sheathing layer or a separate solid segment of polypyrrole. Polypyrrole is a biocompatible conductive polymer. Incorporation of a polypyrrole segment may allow for wiring fuel cells together, connecting them electrically to each other or to other entities within humans or other animals. This may allow the fuel cells to operate in parallel, or in series, with each other or with other devices.

In accordance with at least one embodiment, the functional microparticle may also carry drugs, proteins, nucleic acids, or optically active molecules. These payloads may be carried on the surface of the functional microparticle, adhered via specific binding chemistries. Alternatively, these payloads may be incorporated into the volume of various components of the functional microparticle. The microparticles may emit light, for example by connecting the fuel cell to a light-emitting diode, or by carrying luminol or other fluorescent payloads. This light might be used to activate nerve or other cells.

In one embodiment, the carbon nanotube-nafion composite may include a drug embedded into the volume of the composite. The payload may be loaded into a component of the functional microparticle during the process of making the various layer of the microparticle, or it may be infused into the microparticle after the microparticle has been assembled and released from the working plate. As an example, the payload may be loaded into the tube section by immersing the microparticle in a solution containing the payload. One method of infusing a material, such as a polymer, with a payload such as a drug, is to simply store the material in a solution containing a high concentration of the desired payload.

In accordance with at least one embodiment, the cathode layer may be composed of carbon nanotubes, graphene, or another material suitable for protonation of oxygen to generate water. The carbon nanotubes, graphene, C60, or other material may be filled at an appropriate concentration to ensure the operation of the fuel cell.

The described process is performed on a working piece containing pores. In one embodiment, these pores are cylindrical, parallel to each other, and each has two openings, one on either side of the working piece. The working piece has a conductive layer added, sealing all pores on one side of the working piece. The processes described in this application are intended to be performed on the working piece as a whole, meaning that the process described herein generates one fuel cell for each pore in the working piece. As in anodic aluminum oxide working pieces, pore density may exceed 1 billion pores per square centimeter. Thus, the proposed technique is capable of making at least 1 billion fuel cells simultaneously.

It should be understood that an electrical storage system may be resident in the same particle as the functional microparticle, for example in the form of one or more deposited layers comprising a capacitor. An attached storage system may be added in the form of an additional layer of deposited materials on either ends of the functional microparticle.

It should also be understood that the operations explained herein may be implemented in conjunction with, or under the control of, one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control of the fabrication operations disclosed herein may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

We claim:

1. An apparatus comprised of a functional microparticle with at least one dimension less than fifty microns in length and containing a magnetizable material segment, wherein the microparticle carries a therapeutic payload formed as a tube positioned to surround the magnetizable segment, wherein the tube comprises an electrically insulating material, wherein the apparatus further comprises an anode segment.

2. The apparatus of claim 1, wherein the functional microparticle is a fuel cell that generates electrical current.

3. The apparatus of claim 2, wherein some component of the fuel cell incorporates a sheathing layer or a separate solid segment of polypyrrole.

4. The apparatus of claim 1, wherein the functional microparticle generates radio frequency wave electromagnetic radiation whose frequency changes in response to exposure to an applied magnetic field.

5. The apparatus of claim 4, wherein the functional microparticle is a spin-torque nano-oscillator.

6. The apparatus of claim 1, wherein the functional microparticle carries a therapeutic payload.

7. The apparatus of claim 1, wherein the functional microparticle delivers light energy.

8. The apparatus of claim 1, wherein the functional microparticle is a self-contained fuel cell having the anode, a cathode, a separator membrane, and a magnetic component.

9. The apparatus of claim 8, wherein the fuel cell includes segments for oxidation of glucose and reduction of oxygen.

10. The apparatus of claim 1, wherein the functional microparticle carries drugs, proteins, nucleic acids, or optically active molecules.

11. The apparatus of claim 1, wherein the magnetizable segment is stacked directly beneath the anode segment and the tube surrounds the magnetizable and anode segments.

* * * * *